(12) United States Patent
Lee (10) Patent No.: US 9,351,804 B2
(45) Date of Patent: May 31, 2016

(54) NEEDLE UNIT FOR ENDODONTIC TREATMENT

(76) Inventor: In-Whan Lee, Seoul (KR)

(*) Notice: Subject to any disclaimer, the term of this patent is extended or adjusted under 35 U.S.C. 154(b) by 407 days.

(21) Appl. No.: 12/594,818

(22) PCT Filed: Apr. 4, 2008

(86) PCT No.: PCT/KR2008/001909
§ 371 (c)(1),
(2), (4) Date: Oct. 28, 2009

(87) PCT Pub. No.: WO2008/123700
PCT Pub. Date: Oct. 16, 2008

(65) Prior Publication Data
US 2010/0143862 A1    Jun. 10, 2010

(30) Foreign Application Priority Data

Apr. 5, 2007   (KR) .................. 10-2007-0033890
Apr. 9, 2007   (KR) .................. 10-2007-0034719
Apr. 17, 2007  (KR) .................. 10-2007-0037641
May 31, 2007   (KR) .................. 10-2007-0053062
Apr. 2, 2008   (KR) .................. 10-2008-0030942

(51) Int. Cl.
*A61C 5/02* (2006.01)
*A61C 5/04* (2006.01)

(52) U.S. Cl.
CPC .. *A61C 5/04* (2013.01); *A61C 5/045* (2013.01)

(58) Field of Classification Search
CPC ..... A61C 5/04; A61C 5/045; A61M 39/0606; A61M 39/0693; A61M 25/0097; A61M 39/02; A61M 25/0612; A61M 25/02

USPC ........ 433/80, 81, 89; 604/264, 272, 273, 274, 604/174, 164.08, 164.09, 164.11
See application file for complete search history.

(56) References Cited

U.S. PATENT DOCUMENTS 4,219,618 A * 8/1980 Leonard .......................... 433/80
4,265,618 A * 5/1981 Herskovitz et al. ............. 433/32
(Continued)

FOREIGN PATENT DOCUMENTS

JP   55-037609 U   3/1980
JP   01-077720 U   5/1989
(Continued)

OTHER PUBLICATIONS

European Patent Office, European Search Report for EP Application No. 08741159.1, Jan. 31, 2014.

*Primary Examiner* — Heidi M Eide
(74) *Attorney, Agent, or Firm* — IP Legal Services, LLC (57) ABSTRACT

Provided is a needle unit for endodontic treatment, including a needle bent at predetermined angle; a needle unit body where the needle is rotatably mounted; and an inserter for pressing the needle to fix the needle to the needle unit body. The present invention provides an optimal needle for efficiently realizing a needle unit for endodontic treatment. To be specific, the needle unit can be easily used by an operator because a needle bent at a predetermined angle is rotatably mounted on a needle unit body. Also, a diffuser portion is provided at a proximal end of the needle and pressed by an inserter so that the needle is fixed at a constant pressure. Hence, the needle is not fixed too loosely or too tightly to an extent that much force is required to rotate the needle, so that the operator can easily rotate the needle in a desired direction.

5 Claims, 6 Drawing Sheets

(56) References Cited

U.S. PATENT DOCUMENTS

| | | | |
|---|---|---|---|
| 4,430,081 A * | 2/1984 | Timmermans | 604/256 |
| 4,684,344 A * | 8/1987 | Brockway et al. | 433/81 |
| 5,224,939 A * | 7/1993 | Holman et al. | 604/528 |
| 5,722,829 A | 3/1998 | Wilcox et al. | |
| 5,752,825 A | 5/1998 | Buchanan | |
| 5,876,384 A * | 3/1999 | Dragan et al. | 604/264 |
| 5,897,318 A * | 4/1999 | Badoz | 433/165 |
| 5,934,903 A | 8/1999 | Marlin | |
| 6,066,115 A * | 5/2000 | Chang Lai | 604/110 |
| 6,168,432 B1 * | 1/2001 | Marlin | 433/81 |
| 6,494,713 B1 * | 12/2002 | Pond | 433/81 |
| 2001/0053889 A1 * | 12/2001 | Marggi et al. | 604/164.11 |
| 2004/0009452 A1 * | 1/2004 | Oh | 433/81 |
| 2004/0044313 A1 * | 3/2004 | Nakajima | 604/167.02 |
| 2004/0122378 A1 | 6/2004 | Hsu | |
| 2006/0063126 A1 | 3/2006 | Aloise et al. | |
| 2006/0269893 A1 | 11/2006 | Aloise et al. | |
| 2007/0101797 A1 * | 5/2007 | Quan et al. | 72/416 |
| 2008/0187883 A1 | 8/2008 | Lee et al. | |

FOREIGN PATENT DOCUMENTS

| | | | |
|---|---|---|---|
| JP | 08-131459 A | 5/1996 | |
| JP | 2003-199771 A | 7/2003 | |
| KR | 20-0306002 Y1 | 3/2003 | |
| KR | 20-0427385 Y1 | 9/2006 | |
| KR | 20060104907 A | 10/2006 | |
| KR | 10-2006-0122195 A | 11/2006 | |
| WO | 99/26552 A2 | 6/1999 | |
| WO | 2006/034042 A2 | 3/2006 | |
| WO | 2006/104314 A1 | 10/2006 | |
| WO | WO 2006104314 * | 10/2006 | A61C 5/04 |

* cited by examiner

FIG. 1

-Prior Art-

NEEDLE UNIT FOR ENDODONTIC TREATMENT

CROSS REFERENCES TO RELATED APPLICATIONS

This application is a U.S. national phase application, pursuant to 35 U.S.C. §371, of PCT/KR2008/001909, filed Apr. 4, 2008, designating the United States, which claims priority to Korean Application No. 10-2007-0033890, filed on Apr. 5, 2007; Korean Application No. 10-2007-0034719, filed on Apr. 9, 2007; Korean Application No. 10-2007-0037641, filed on Apr. 17, 2007, and Korean Application No. 10-2007-0053062, filed on May 31, 2007; and Korean Application No. 10-2008-0030942, filed on Apr. 2, 2008. The entire contents of the aforementioned patent applications are incorporated herein by this reference.

TECHNICAL FIELD

The present invention relates to a needle unit for endodontic treatment. The needle unit includes a needle bent at a predetermined angle and including a diffuser portion at a proximal end, a needle unit body where the needle is inserted and mounted rotatably, and an inserter inserted into the needle unit body and pressing the diffuser portion of the needle to fix the needle to the needle unit body. In addition, the present invention relates to an optimal needle for implementation of efficient endodontic treatment.

BACKGROUND ART

According to treatment of a decayed and/or infected tooth done in a dental clinic setting, the decayed portion of the tooth is first removed with a dental handpiece. When the pulp of the tooth is injured, the injured or affected pulp is removed. A root canal is sealed by filling the root canal chamber of the injured pulp with a filler (endodontic cement or sealer), and a prosthetic treatment is then performed on the tooth. In the root canal filling procedure, gutta-percha cones are used as a temporary filling material having an auxiliary function for enabling the filler to penetrate into the root canal and thus to seal up the root canal. Gutta-percha, which is a natural vegetable extract, has a semi-solid phase at room temperature, but has the form of a solid gum when it is compressed or heated. This is called "white gutta-percha."

In endodontic treatment of a decayed tooth, the affected pulp of the tooth is first prepared to remove affected nerve tissues. Thereafter, filler is coated on a root canal wall in order to prevent the root canal from being further affected by another source of infected area. A gutta-percha cone having a suitable size is then inserted into the root canal to fix the filler to the main and accessory portions of the root canal.

With a conventional endodontic instrument, a needle is not bent. Thus, the operator bends the needle in a desired treatment direction when he/she performs a dental treatment, and the operator bends the needle in an opposite direction when he/she performs a dental treatment in an opposite direction. If the needle is bent during use, a thin film of the needle may be cracked or separated. If the operator loosens the needle, turns it in an opposite direction and then re-fixes it in order to avoid the re-bending of the needle after performing the dental treatment in one direction, the already heated needle is difficult to manipulate. The gutta-percha may leak out during the procedure of loosing and re-fixing the needle. The manipulation of the needle is troublesome.

To solve such a problem, Korean Patent Application No. 10-2005-0044248, entitled "Complete melting type wireless charger for endodontic treatment, was filed by the present inventor.

Figure 1:
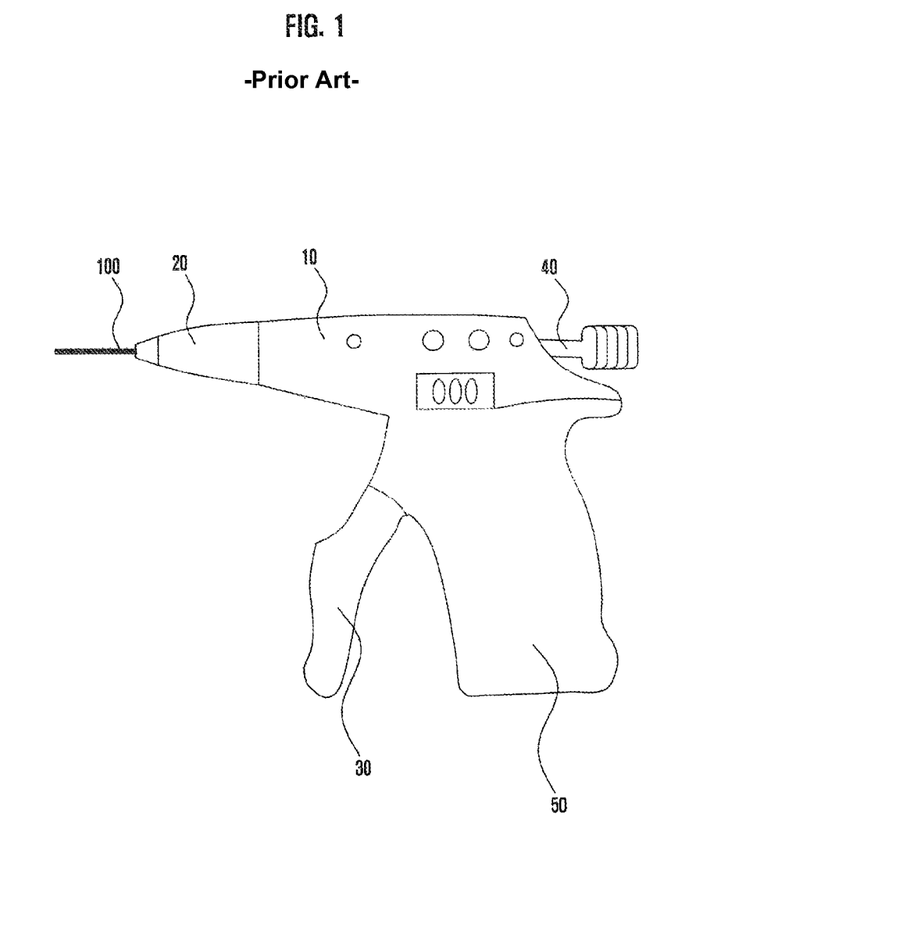
FIG. 1 is a front view schematically illustrating a conventional endodontic instrument.

More specifically, as illustrated in FIG. 1, the endodontic instrument, filed by the present inventor, includes a main body 10, a heater 20, a charge switch 30, an injection member 40, a grasp unit 50, and a needle unit 100. A power supply is built in the main body 10, and the injection member 40 is operated by the manipulation of the charge switch 30. The injection member moves the mounted gutta-percha to the needle unit 100.

Figure 2:
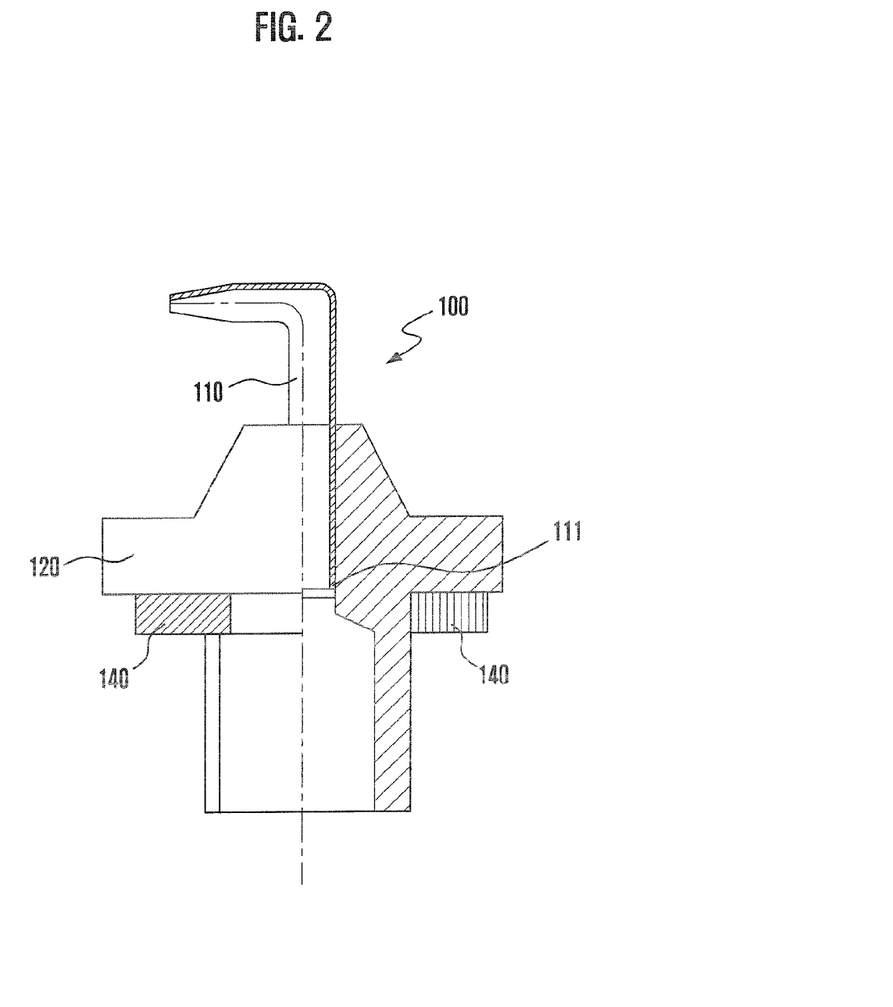
FIG. 2 is a sectional view schematically illustrating a needle unit of the endodontic instrument of FIG. 1.

In addition, as illustrated in FIG. 2, the needle unit 100 includes a needle 110, a needle unit body 120, and a sealing member 140. The needle 110 discharges the molten gutta-percha to a desired location. The needle 110 is bent at a predetermined angle in order for an operator's more convenient working and includes a silver alloy pipe combined with copper alloy or SUS.

A proximal end where the needle 110 is connected to the needle unit body 120 is about 0.9 mm in diameter. A distal end is tapered for suitable dental treatment and is about 0.5 mm to 0.9 mm in diameter. In order to rotatably connect the needle 100 to the needle unit body 120, a rectangular coupling portion 111 having a larger diameter than the needle is formed at the proximal end of the needle connected to the needle unit body.

The needle unit body 120 includes a screw coupling unit on an outer periphery such that it can be connected to the main body. A rectangular coupling groove corresponding to the rectangular coupling portion 111 of the needle is formed inside the needle unit body 120. When the rectangular coupling portion of the needle is inserted into and connected to the rectangular coupling groove of the needle unit body, the needle is 360-degree rotatable, so that the operator can use the needle while rotating it at a desired angle.

However, it is difficult to perform a process of forming the rectangular coupling groove inside the needle unit body. The needle may not be well rotated due to the attachment force generated according to the coupling degree between the rectangular coupling portion and the rectangular coupling groove. If the coupling degree between the rectangular coupling portion and the rectangular coupling groove is too loose, the needle may be easily rotated in an unintended direction. Furthermore, the needle may be released from the needle unit boy 120.

DISCLOSURE

Technical Problem

An embodiment of the present invention is directed to providing a needle unit for endodontic treatment, which can facilitate a dental treatment and can be easily used by an operator because a needle bent at a predetermined angle is rotatably mounted on a needle unit body.

Another embodiment of the present invention is directed to providing a needle unit for endodontic treatment, which can enable the operator to easily rotate a needle in a desired direction. Specifically, a diffuser portion is provided at a proximal end of the needle and is pressed by an inserter, so that the needle is fixed at a constant pressure. Hence, the needle is not fixed too loosely or too tightly to the extent that much force is required to rotate the needle.

Further another embodiment of the present invention is directed to providing an optimal needle having the improved heat transfer efficiency for implementation of efficient endodontic treatment.

Other objects and advantages of the present invention can be understood by the following description, and become apparent with reference to the embodiments of the present invention. Also, it is obvious to those skilled in the art of the present invention that the objects and advantages of the present invention can be realized by the means as claimed and combinations thereof.

Technical Solution

In accordance with an aspect of the present invention, there is provided a needle unit for endodontic treatment, which includes: a needle bent at a predetermined angle; a needle unit body where the needle is rotatably mounted; and an inserter for pressing the needle to fix the needle to the needle unit body.

In accordance with another aspect of the present invention, there is provided a needle unit for endodontic treatment, which includes: a needle bent at a predetermined angle and including a diffuser portion at a proximal end; a needle unit body where the needle is inserted and mounted rotatably; and an inserter inserted into the needle unit body and pressing the diffuser portion of the needle to fix the needle to the needle unit body.

Advantageous Effects

In accordance with the present invention, a needle unit for endodontic treatment can facilitate a dental treatment and can be easily used by an operator because a needle bent at a predetermined angle is rotatably mounted on a needle unit body. Also, a diffuser portion is provided at a proximal end of the needle and is pressed by an inserter, so that the needle is fixed at a constant pressure. Hence, the needle is not fixed too loosely or too tightly to the extent that much force is required to rotate the needle, so that the operator can easily rotate a needle in a desired direction. Furthermore, since the whole shape of the needle is tapered from the proximal end to the distal end, materials flowing inside can be easily discharged without friction, and the processing is easily. Moreover, there is provided an optimal needle having the improved heat transfer efficiency for implementation of efficient endodontic treatment.

BEST MODE FOR THE INVENTION

The advantages, features and aspects of the invention will become apparent from the following description of the embodiments with reference to the accompanying drawings, which is set forth hereinafter.

According to a first embodiment of the present invention devised to achieve the above objects, a needle unit for endodontic treatment includes: a needle bent at a predetermined angle; a needle unit body where the needle is rotatably mounted; and an inserter for pressing the needle to fix the needle to the needle unit body.

According to a second embodiment of the present invention, a needle unit for endodontic treatment includes: a needle bent at a predetermined angle and including a diffuser portion at a proximal end; a needle unit body where the needle is inserted and mounted rotatably; and an inserter inserted into the needle unit body and pressing the diffuser portion of the needle to fix the needle to the needle unit body.

The needle may include a tapered portion at a distal end for facilitating discharge of gutta-percha.

The diffuser portion may have a diameter of 0.9 mm to 5 mm, and the tapered portion has a diameter of 0.5 mm to 0.9 mm.

The inserter may form a gutta-percha passage there inside, the inserter including: a pressing portion corresponding to the diffuser portion at the front; and a stepped portion formed on an outer surface of the inserter to restrict an insertion direction movement toward the needle unit body.

The needle unit body may include a receiving portion for receiving the needle and the inserter, and a screw coupling portion connected to a main body of an endodontic instrument, the receiving portion including a stepped portion formed corresponding to size and shape of the received needle and inserter to restrict a pressing direction movement of the inserter.

The needle unit body may be made of brass and formed in a hexagonal rod shape.

The needle unit may further include a sealing member mounted between the needle unit body and a main body of an endodontic instrument.

According to a third embodiment of the present invention, a needle unit for endodontic treatment includes: a needle including a diffuser portion at a proximal end; a needle body unit where the needle is mounted; and an inserter inserted into the needle unit body and pressing the diffuser portion of the needle to fix the needle to the needle unit body.

According to a fourth embodiment of the present invention, a needle unit for endodontic treatment may include: a needle including a flange portion at a proximal end; a needle unit body where the needle is inserted and mounted; and an inserter inserted into the needle unit body and pressing the flange portion of the needle to fix the needle to the needle unit body.

The needle unit of claim 10, wherein the inserter further includes a head inserter for forwardly inserting the flange portion of the needle into the needle unit body, and the flange portion of the needle is fixed between the head inserter and the inserter.

According to a first embodiment of the present invention, the needle may be constantly tapered from the proximal end to the distal end.

According to a second embodiment of the present invention, the needle may include: a tapered portion having a proximal end inserted into the needle unit body and having the largest inner diameter, the tapered portion being tapered such that an inner diameter is constantly decreased up to a predetermined location in a length direction of the needle; and a test rate portion extending from a distal end of the tapered portion and having a constant inner diameter.

According to a third embodiment of the present invention, the needle includes: a straight portion having a proximal end inserted into the needle unit body and having a constant inner diameter; and a tapered portion extending from the straight portion and tapered such that an inner diameter is constantly decreased.

According to a fourth embodiment of the present invention, the needle may have a constant inner diameter.

According to a fifth embodiment of the present invention, the needle may include: an inner pipe having a straight shape extending with a constant inner diameter; and an outer pipe having a straight shape covering a predetermined section of the inner pipe and extending a constant inner diameter, the outer pipe being inserted into the needle unit body.

According to a sixth embodiment of the present invention, the needle includes: an inner pipe including a straight portion extending with a constant inner diameter, and a tapered portion constantly tapered; and an outer pipe having a straight shape covering the straight portion of the inner pipe and extending with a constant inner diameter.

According to a seventh embodiment of the present invention, the needle may include: a first pipe having a straight shape extending in a length direction with a constant diameter; a second pipe having a straight shape extending in a length direction with a constant diameter, the second pipe having an inner diameter corresponding to an outer diameter of the first pipe, the second pipe having a distal end to which a proximal end of the first pipe is inserted and connected; and a third pipe having a straight shape extending in a length direction with a constant diameter, the third pipe having an inner diameter corresponding to an outer diameter of the second pipe, the third pipe having a distal end to which a proximal end of the second pipe is inserted and connected.

The first pipe and the second pipe may be made of copper or copper alloy, and the third pipe is made of aluminum or aluminum alloy.

The first pipe may have the outer diameter of 0.03 mm to 0.07 mm; the second pipe has the outer diameter of 0.05 mm to 0.07 mm; and the third pipe has the outer diameter of 0.07 mm to 0.12 mm.

Preferably, the first pipe has the outer diameter of 0.051 mm; the second pipe has the outer diameter of 0.07 mm; and the third pipe has the outer diameter of 0.09 mm.

Hereinafter, the construction, function and effect of the needle unit for endodontic treatment in accordance with preferable embodiments of the present invention will be described in detail.

Figure 3:
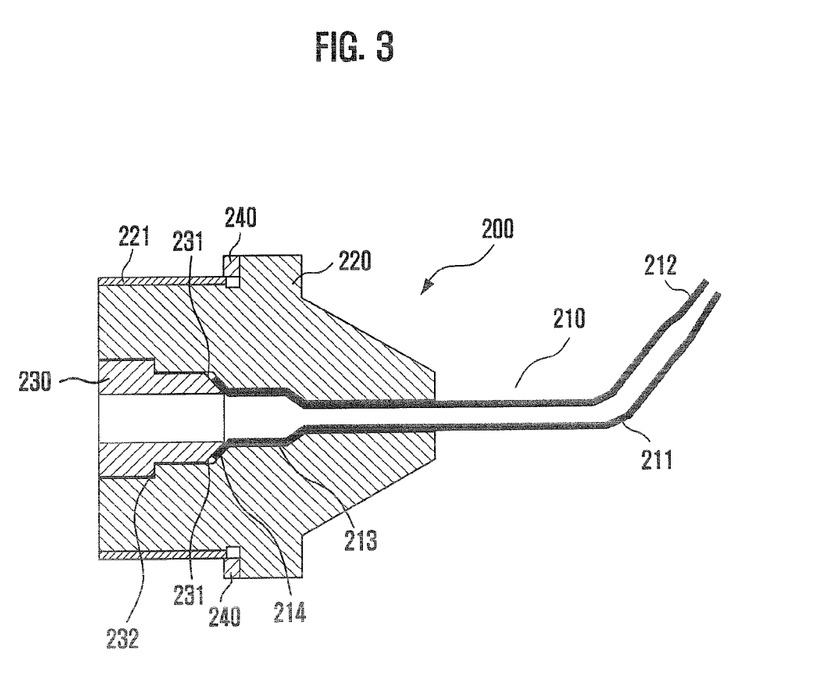
FIG. 3 is a sectional view schematically illustrating a first embodiment of a needle unit for endodontic treatment in accordance with the present invention.

FIG. 3 is a sectional view schematically illustrating a needle unit for endodontic treatment in accordance with the present invention. As illustrated, the needle unit 200 for endodontic treatment in accordance with the present invention includes a needle 210, a needle unit body 220, and an inserter 230. The needle 210 is formed in a pipe shape and discharges the molten gutta-percha to a desired location. The needle 210 includes a bending portion 211 bent at a predetermined angle to facilitate the dental treatment, and a tapered portion 212 disposed at a distal end of the bent needle for facilitate the discharge of the gutta-percha. Also, the needle 210 includes a diffuser portion 214 at a proximal end of the needle 210 that is inserted into the needle unit body 220. The diffuser portion 214 of the needle 210 has a diameter of about 0.9 mm to about 3 mm, preferably 1.5 mm. In addition, it is preferable that the tapered portion 212 has a diameter of about 0.5 mm to about 0.9 mm.

In accordance with another embodiment of the present invention, the diffuser portion may be formed in various shapes as illustrated in FIG. 3.

The inserter 230 is inserted into the needle unit body 220 to press the diffuser portion 214 of the needle 210. A gutta-percha passage is formed inside the inserter 230. A pressing portion 231 corresponding to the diffuser portion is formed in front of the inserter 230. A stepped portion 231 for restricting an insertion direction movement of the inserter 230 is formed on the outer surface of the inserter 230.

The needle unit body 220 includes a receiving portion for receiving the needle 210 and the inserter 230, and a screw coupling portion 221 connected to the main body of the endodontic instrument. The receiving portion is formed corresponding to size and shape of the needle 210 and the inserter 230. In the receiving portion, a stepped portion for restricting a press direction movement of the inserter 230 is formed corresponding to the stepped portion of the inserter. Accordingly, the needle 210 and the inserter 230 are received in the needle unit body 220. A predetermined pressure and interval are maintained when the pressing portion 231 of the inserter 230 presses the diffuser portion 214 of the needle on the same axis.

More specifically, when the stepped portion 232 of the inserter 230 comes in contact with the stepped portion of the receiving portion, the press direction movement of the inserter is restricted and the inserter is moved by a preset location to press the needle at a predetermined pressure.

In addition, it is preferable that the needle unit body 220 is made of brass in order for excellent processability and heat conductivity, and it is formed in a hexagonal rod shape in order for easy connection with the main body. Furthermore, it is preferable that the inserter 230 is made of brass in order for excellent processability and heat conductivity, and it is inserted into the diffuser portion 231 of the needle in order for preventing leakage of the gutta-percha.

The needle unit 200 for endodontic treatment in accordance with the present invention further includes a washer 240 as a sealing member. The washer 240 is provided for preventing leakage of high-temperature gutta-percha and is made of gasket robust against high heat. The washer 240 is disposed in front of the screw coupling portion 221 of the needle unit body 220. Therefore, the washer 240 tightly connects the needle unit body 220 to the main body and prevents the leakage of the gutta-percha.

In the needle unit 200 for endodontic treatment in accordance with the present invention, the inserter 230 can press the needle 210 at a preset pressure. Hence, the operator can easily rotate the needle in a desired direction, the needle is not fixed too loosely or too tightly to the extent that much force is required to rotate the needle.

Figure 4:
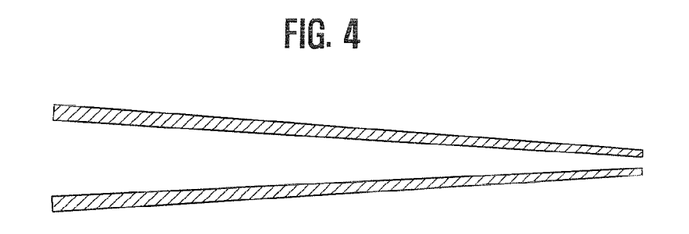
FIG. 4 is a sectional view schematically illustrating a first embodiment of a needle in accordance with the present invention.

FIG. 4 is a sectional view schematically illustrating a first embodiment of the need in accordance with the present invention. As illustrated in FIG. 4, the needle has a tapered shape such that it has the largest inner diameter at the proximal end of the needle, which is inserted into the needle unit body, and has the smallest inner diameter at the distal end. It is preferable that the needle is thicker at the proximal end than at the other end.

Figure 5:
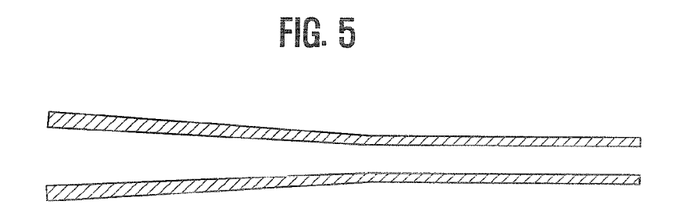
FIG. 5 is a sectional view schematically illustrating a second embodiment of a needle in accordance with the present invention.

FIG. 5 is a sectional view schematically illustrating a second embodiment of the needle in accordance with the present invention. As illustrated in FIG. 5, the needle includes a tapered portion and a straight portion. A proximal end of the tapered portion is inserted into the needle unit body and has the largest inner diameter. The tapered portion is tapered such that its inner diameter is constantly decreased up to the other end corresponding to a predetermined location in a length direction of the needle. The straight portion is connected to the distal end of the tapered portion and has a constant inner diameter. It is preferable that the needle is thicker at the proximal end than at the distal end, and the straight portion has the same thickness as the distal end of the tapered portion.

Figure 6:
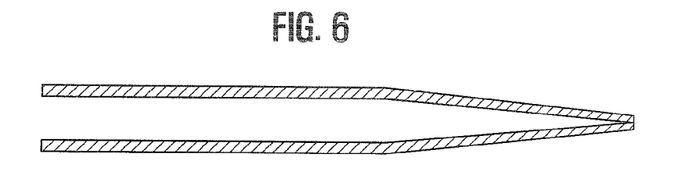
FIG. 6 is a sectional view schematically illustrating a third embodiment of a needle in accordance with the present invention.

FIG. 6 is a sectional view schematically illustrating a third embodiment of the needle in accordance with the present invention. As illustrated in FIG. 6, the needle includes a straight portion and a tapered portion. A proximal end of the straight portion is inserted into the needle unit body and has the largest inner diameter. The inner diameter of the straight portion constantly extends up to the proximal end of the tapered portion corresponding to a predetermined location in a length direction of the needle. The tapered portion is connected to a distal end of the straight portion and is tapered such that its inner diameter is gradually decreased. In addition, it is preferable that the straight portion is thicker than the distal end of the tapered portion.

Figure 7:
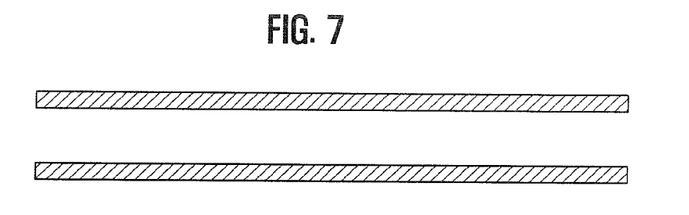
FIG. 7 is a sectional view schematically illustrating a fourth embodiment of a needle in accordance with the present invention.

FIG. 7 is a sectional view schematically illustrating a fourth embodiment of the needle in accordance with the present invention. As illustrated in FIG. 7, the needle is straight such that its inner diameter is constant.

The above-described needles may further include a heat accumulating portion at a predetermined location in a length direction. The heat accumulating portion temporarily accumulates heat from the proximal end of the needle and transfers the accumulated heat to the distal end of the needle, thereby achieving more efficient heat transfer.

In addition, the needle unit includes the needle having the diffuser portion at the proximal end, the needle unit body inserted and mounted to make the needle rotatable, and the inserter inserted into the needle unit body and pressing the diffuser portion of the needle to fix the needle to the needle unit body. The needle is tapered from the proximal end to the distal end.

Figure 8:
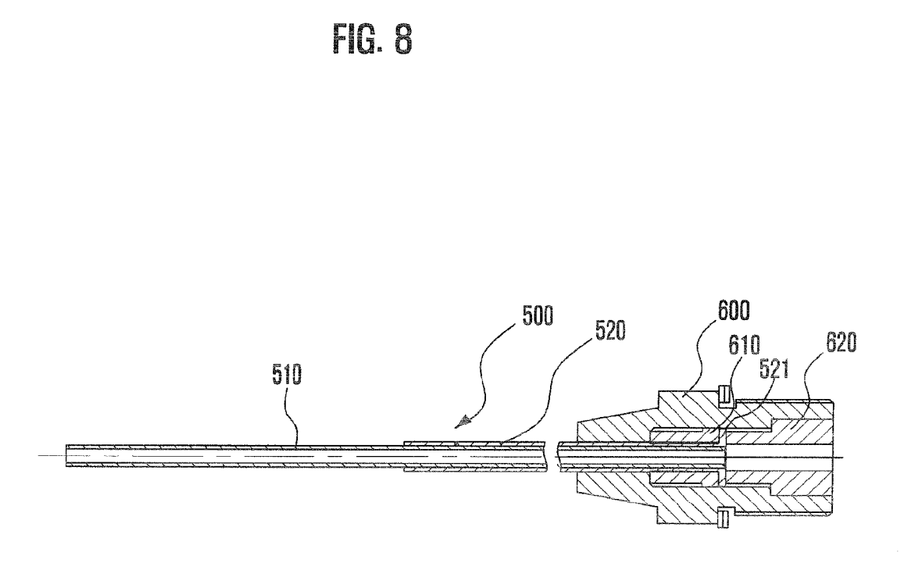
FIG. 8 is a sectional view schematically illustrating a fifth embodiment of a needle and a needle unit in accordance with the present invention.

FIG. 8 is a sectional view schematically illustrating a fifth embodiment of the needle and a needle structure in accordance with the present invention. As illustrated in FIG. 8, the needle 500 includes an outer pipe 520 and an inner pipe 510. The outer pipe 520 is connected to the main body of the endodontic instrument through a head 600 that is rotatably connected. More specifically, the outer pipe 520 and the head 600 are connected as follows. First, a fixing flange portion 521 is formed at a proximal end of the outer pipe 520 and is connected to a head inserter 610 inside the head 600 by press fit or welding. In addition, the head inserter 610 is located inside the head 600 and rotated within the head together with the outer pipe 520. Furthermore, the head 600 includes an inserter 620 for fixing the head inserter 610 in order to prevent the head inserter 610 from being released to the outside of the head. Accordingly, the flange portion 521 of the outer pipe 520 is fixed between the head inserter 610 and the inserter 620.

Moreover, the outer pipe is formed in a straight shape having a constant diameter and extending in a length direction and is made of copper or silver alloy.

The inner pipe 510 is formed a straight shape having an outer diameter corresponding to the inner diameter of the outer pipe 520 and extending in a length direction. The inner pipe 510 is made of SUS or aluminum alloy. The inner pipe is inserted into and tightly connected to the outer pipe such that the outer pipe 520 encloses a predetermined outer section of the inner pipe 510. The connection structure of the inner pipe and the outer pipe made of different metal can transfer heat more efficiently. It is preferable that the inner pipe has 23 gauge where the inner diameter is 0.41 mm and the outer diameter is 0.64 mm, and has a thickness of about 0.05 mm. As the inner pipe is formed to have the constant thickness of about 0.05 mm and the constant inner diameter of 0.41 mm, it receives less pressure than an existing product when it is pressed.

Figure 9:
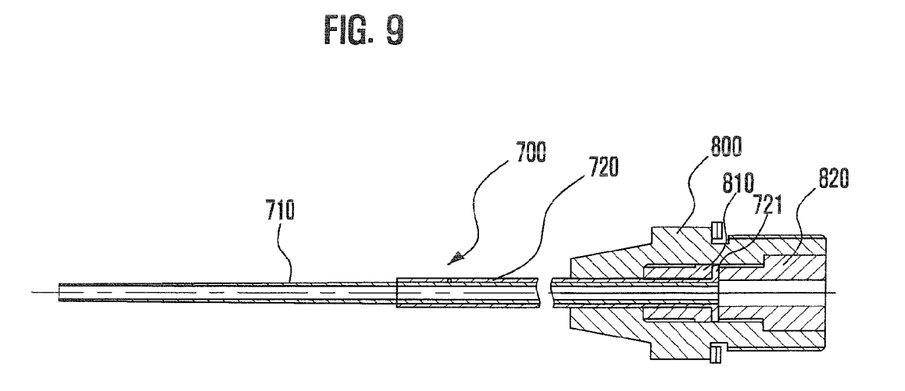
FIG. 9 is a sectional view schematically illustrating a sixth embodiment of a needle and a needle unit in accordance with the present invention.

FIG. 9 is a sectional view schematically illustrating a sixth embodiment of the needle and a needle structure in accordance with the present invention. As illustrated in FIG. 9, the needle 700 in accordance with the present invention includes an outer pipe 720 and an inner pipe 710. The outer pipe 720 is connected to the main body of the endodontic instrument through a head 800 that is rotatably connected.

More specifically, the outer pipe 720 and the head 800 are connected as follows. First, a proximal end of the outer pipe 720 is a flange portion 721 serving as a fixing portion and is connected to a head inserter 810 inside the head 800 by press fit or welding. In addition, the head inserter 810 is located inside the head 800 and rotated within the head together with the outer pipe 720. Furthermore, the head 800 includes an inserter 820 for fixing the head inserter 810 in order to prevent the head inserter 810 from being released to the outside of the head.

The outer pipe is formed in a straight shape having a constant diameter and extending in a length direction and is made of copper or silver alloy.

The inner pipe 710 is formed in a straight portion having a constant diameter and extending in a length direction, and a tapered portion having a constantly decreasing outer diameter. The straight portion is formed at a proximal end of the inner pipe, and the tapered portion is formed at a distal portion of the inner pipe. In addition, the straight portion of the inner pipe has an outer diameter corresponding to an inner diameter of the outer pipe. The straight portion of the inner pipe is inserted into the outer pipe and is tightly connected such that the outer pipe 720 encloses the straight portion of the inner pipe. Furthermore, the inner pipe 710 is made of SUS or aluminum alloy. The connection structure of the inner pipe and the outer pipe made of different metal can transfer heat more efficiently. The inner pipe has 25 gauge where the inner diameter is 0.1 mm to 0.5 mm, preferably 0.30 mm, and the outer diameter is 0.3 mm to 0.70 mm, preferably 51 mm.

Figure 10:
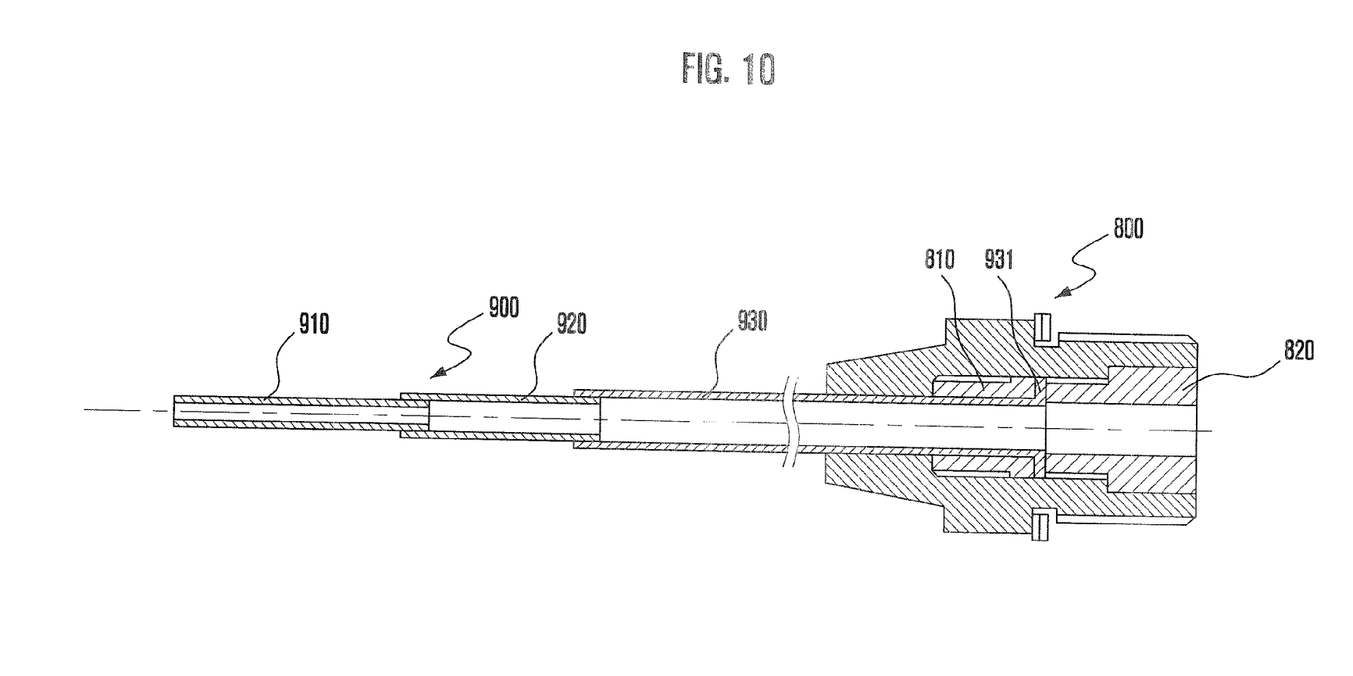
FIG. 10 is a sectional view schematically illustrating a seventh embodiment of a needle and a needle unit in accordance with the present invention.

FIG. 10 is a sectional view schematically illustrating a seventh embodiment of the needle and a needle structure in accordance with the present invention. The needle 900 in accordance with the present invention includes a first pipe 910, a second pipe 920, and a third pipe 930. The third pipe 930 is connected to the main body of the endodontic instrument through a head 800 that is rotatably connected.

More specifically, the outer pipe 720 and the head 800 are connected as follows. First, a proximal end of the third pipe 930 is a flange portion 931 and is connected to a head inserter 810 inside the head 800 by press fit or welding. In addition, the head inserter 810 is located inside the head 800 and rotated within the head together with the outer pipe 930.

Furthermore, the head 800 includes an inserter 820 for fixing the head inserter 810 in order to prevent the head inserter 810 from being released to the outside of the head.

The first pipe 910 is formed in a straight shape having a constant diameter and extending in a length direction and is made of copper or copper alloy. The second pipe 920 is formed in a straight shape having a constant diameter and extending in a length direction and is made of copper or copper alloy. The third pipe 930 is formed in a straight shape having a constant diameter and extending a length direction and is made of aluminum or aluminum alloy.

The outer diameter of the first pipe 910 corresponds to the inner diameter of the second pipe 920, and the outer diameter of the second pipe 920 corresponds to the inner diameter of the third pipe 930. The proximal end of the first pipe is inserted into and tightly connected to the distal end of the second pipe, and the proximal end of the second pipe is inserted into and tightly connected to the distal end of the second pipe. Furthermore, in order to increase the coupling force, the coupling portions of the first pipe 910, the second pipe 920, and the third pipe 930 are coupled by brazing or welding.

Furthermore, the first pipe 910 has the outer diameter of 0.03 mm to 0.07 mm; the second pipe 920 has the outer diameter of 0.05 mm to 0.07 mm; and the third pipe 930 has the outer diameter of 0.07 mm to 0.12 mm. Preferably, the first pipe 910 has the outer diameter of 0.051 mm; the second pipe 920 has the outer diameter of 0.7 mm; and the third pipe 930 has the outer diameter of 0.09 mm.

The connection structure of the first and second pipes made of the same kind of a metal and the third pipe made of a different kind of a metal can transfer heat more efficiently.

While the present invention has been described with respect to the specific embodiments, it will be apparent to those skilled in the art that various changes and modifications may be made without departing from the spirit and scope of the invention as defined in the following claims.

What is claimed is:

1. A needle unit for endodontic treatment, comprising:
   a needle unit body including a receiving portion therein that has a stepped portion;
   a needle including a bent portion bent at a predetermined angle at a predetermined portion thereof, and a diffuser portion at a proximal end thereof, wherein the needle is formed of a metal material, and the diffuser portion includes an obliquely stepped structure configured to provide a gutta-percha passage and to come in contact with a portion of the receiving portion of the needle unit body, wherein the diffuser portion includes (i) an inlet portion having a diameter gradually increased toward the proximal end of the needle, (ii) an outlet portion having a diameter gradually reduced toward a distal end of the outlet portion, and (iii) a middle portion which is positioned between the inlet and outlet portions and has a constant diameter, and wherein the diameter of the inlet portion is greater than the diameter of the middle portion, and the diameter of the middle portion is greater than the diameter of the outlet portion; and
   an inserter forming a gutta-percha passage thereinside and including a pressing portion at a distal end thereof and a stepped portion at an outer surface thereof, the pressing portion adjacent to and in contact with the inlet portion of the diffuser portion at the proximal end of the needle so that the inlet portion of the diffuser portion is sandwiched between the pressing portion and an inner surface of the needle unit body,
   wherein the needle and the inserter are received in the receiving portion of the needle unit body such that the needle projects out of the needle unit body through an opening in the needle unit body, the proximal end of the needle is pressed adjacently against the distal end of the inserter, the needle unit body surrounds both the proximal end of the needle and the distal end of the inserter, and the stepped portion of the inserter comes in contact with the stepped portion of the receiving portion, and
   wherein the inserter is configured to press the inlet portion of the diffuser portion of the needle such that (i) the inner surface of the receiving portion comes in contact with the outer surface of the received needle and inserter and (ii) a movement of the needle is restricted in a pressing direction of the inserter and is allowable in a rotation direction of the needle.

2. The needle unit of claim 1, wherein the needle unit body is made of brass and formed in a hexagonal rod shape.

3. The needle unit of claim 1, wherein the needle unit body includes a screw coupling portion at an outer surface thereof.

4. The needle unit of claim 1, wherein the needle includes a tapered portion at a distal end of the needle.

5. The needle unit of claim 4, wherein the diffuser portion has a diameter of 0.9 mm to 5 mm, and the tapered portion has a diameter of 0.5 mm to 0.9 mm.

\* \* \* \* \*